(12) United States Patent
Shimakura

(10) Patent No.: US 12,386,422 B2
(45) Date of Patent: Aug. 12, 2025

(54) OPERATION CONTROL DEVICE, OPERATION CONTROL METHOD, AND NON-TRANSITORY STORAGE MEDIUM

(71) Applicant: JVCKENWOOD Corporation, Yokohama (JP)

(72) Inventor: Takamitsu Shimakura, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 0 days.

(21) Appl. No.: 18/413,086

(22) Filed: Jan. 16, 2024

(65) Prior Publication Data

US 2024/0152207 A1    May 9, 2024

Related U.S. Application Data

(63) Continuation of application No. PCT/JP2022/010732, filed on Mar. 10, 2022.

(30) Foreign Application Priority Data

Jul. 20, 2021   (JP) ................. 2021-119291

(51) Int. Cl.
    *G06F 3/01*    (2006.01)
(52) U.S. Cl.
    CPC .................. *G06F 3/015* (2013.01)
(58) Field of Classification Search
    None
    See application file for complete search history.

(56) References Cited

U.S. PATENT DOCUMENTS

| | | | | |
|---|---|---|---|---|
| 2010/0010365 A1* | 1/2010 | Terao | .......... | G01C 21/367 600/544 |
| 2013/0063550 A1* | 3/2013 | Ritchey | .......... | A61B 5/7246 345/207 |

(Continued)

FOREIGN PATENT DOCUMENTS

| | | |
|---|---|---|
| JP | 2011-150672 | 8/2011 |
| JP | 2013-117957 | 6/2013 |

(Continued)

OTHER PUBLICATIONS

International Search Report and Written Opinion for International Application No. PCT/JP2022/010732 mailed on Apr. 26, 2022, 8 pages.

(Continued)

*Primary Examiner* — Parul H Gupta
(74) *Attorney, Agent, or Firm* — Amin, Turocy & Watson, LLP

(57) ABSTRACT

An operation control device includes: a brain information acquiring unit configured to acquire brain information of a user; a determining unit configured to determine whether or not the brain information acquired by the brain information acquiring unit represents brain information corresponding to a first command and a second command which are different from each other; an information presenting unit configured to present information which evokes the second command to the user; and an executing unit configured to execute operation specified in the first command when the determining unit determines that the brain information corresponding to the second command is acquired after acquiring the brain information corresponding to the first command.

5 Claims, 4 Drawing Sheets

(56) References Cited

U.S. PATENT DOCUMENTS

| | | | |
|---|---|---|---|
| 2013/0138248 A1 | 5/2013 | Mathan et al. | |
| 2015/0338917 A1* | 11/2015 | Steiner | H04M 1/72412 345/156 |
| 2021/0173367 A1 | 6/2021 | Sato et al. | |

FOREIGN PATENT DOCUMENTS

| | | |
|---|---|---|
| JP | 2018-190164 | 11/2018 |
| JP | 2021-089636 | 6/2021 |

OTHER PUBLICATIONS

Extended European Search Report for European Patent Application No. 22845620.8 dated Sep. 30, 2024.

Perego Paolo et al: "Psychometric Evaluation with Brain-Computer Interface", Jul. 9, 2011 (Jul. 9, 2011), SAT 2015 18th International Conference, Austin, TX, USA, Sep. 24-27, 2015; [Lecture Notes in Computer Science; Lect.Notes Computer], Springer, Berlin, Heidelberg, pp. 406-413, XP047433131, ISBN: 978-3-540-74549-5.

* cited by examiner

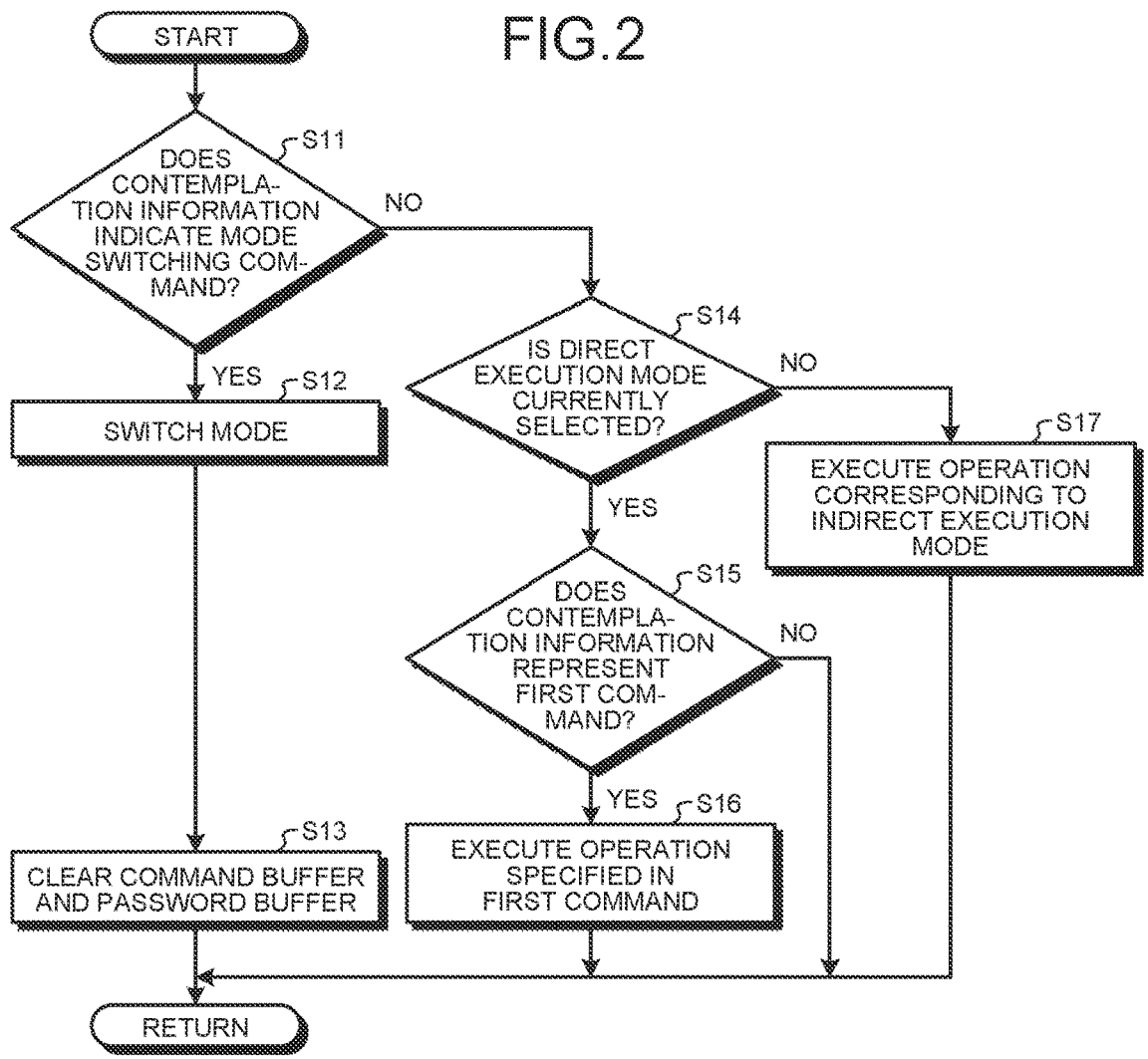
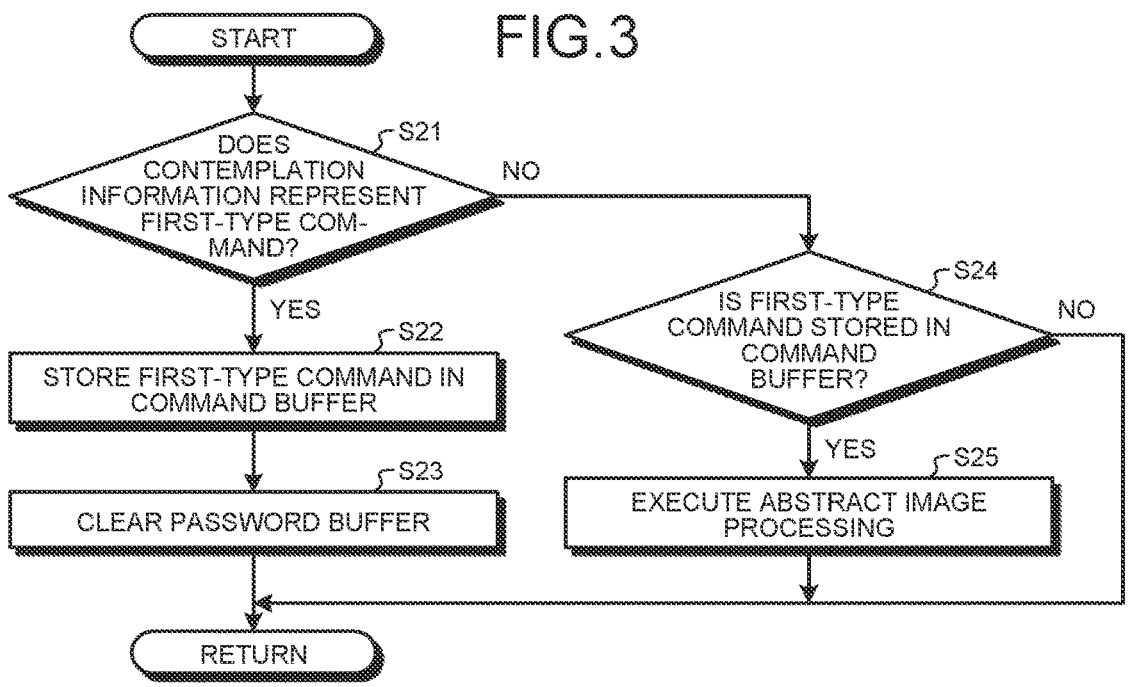

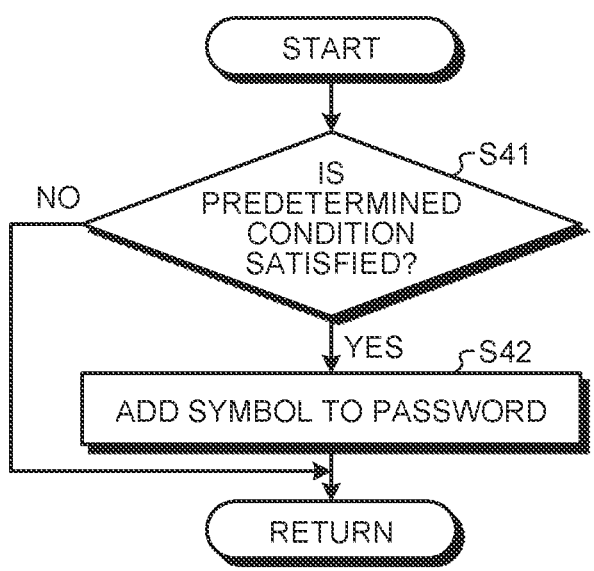

OPERATION CONTROL DEVICE, OPERATION CONTROL METHOD, AND NON-TRANSITORY STORAGE MEDIUM

CROSS-REFERENCE TO RELATED APPLICATIONS

This application is a Continuation of PCT International Application No. PCT/JP2022/010732 filed on Mar. 10, 2022 which claims the benefit of priority from Japanese Patent Application No. 2021-119291 filed on Jul. 20, 2021, the entire contents of both of which are incorporated herein by reference.

BACKGROUND OF THE INVENTION

The application concerned is related to an operation control device, an operation control method, and a non-transitory storage medium.

In recent years, there has been advancement in a technology for measuring information about the brain, and a brain-machine-interface (BMI) is becoming more and more realistic as an interface for directly linking the brain and a machine. As an example of such a technology, a technology disclosed in Patent Literature 1 is known. According to Japanese Patent Application Laid-open No. 2013-117957, when a user receives any stimulus, a plurality of steady-state visual-evoked response potential signals is acquired from the user, and system command signals are provided.

In a conventional BMI, at a time of execution of a brain wave command, if there is any irrelevant stimulus, then the stimulus may appear in the brain waves to implement some commands. For example, in a case of a forward movement command by which the robot moves forward when "forward movement" is wished for a robot, if any person present around merely says the term "forward movement", the brain arbitrarily evokes the "forward movement" and the forward movement command gets issued. Moreover, if the robot is operated while an operator thereof is looking at its movement, when a situation in which the robot is moving forward is displayed on a monitor, the brain of the operator who is looking at the monitor arbitrarily keeps on evoking "forward movement", and accordingly the forward movement commands get arbitrarily issued.

SUMMARY OF THE INVENTION

An operation control device, an operation control method, and a non-transitory storage medium are disclosed.

According to one aspect of the present application, there is provided an operation control device comprising: a brain information acquiring unit configured to acquire brain information of a user; a determining unit configured to determine whether or not the brain information acquired by the brain information acquiring unit represents brain information corresponding to a first command and a second command which are different from each other; an information presenting unit configured to present information which evokes the second command to the user; and an executing unit configured to execute operation specified in the first command when the determining unit determines that the brain information corresponding to the second command is acquired after acquiring the brain information corresponding to the first command.

According to one aspect of the present application, there is provided an operation control method comprising: acquiring brain information of a user; determining whether or not the acquired brain information represents brain information corresponding to a first command and a second command which are different from each other; presenting information which evokes the second command to the user; and executing operation specified in the first command when it is determined that the brain information corresponding to the second command is acquired after acquiring the brain information corresponding to the first command.

According to one aspect of the present application, there is provided a non-transitory storage medium that stores a program that causes a computer to execute: acquiring brain information of a user; determining whether or not the acquired brain information represents brain information corresponding to a first command and a second command which are different from each other; presenting information which evokes the second command to the user; and executing operation specified in the first command when it is determined that the brain information corresponding to the second command is acquired after acquiring the brain information corresponding to the first command.

The above and other objects, features, advantages and technical and industrial significance of this application will be better understood by reading the following detailed description of presently preferred embodiments of the application, when considered in connection with the accompanying drawings.

BRIEF DESCRIPTION OF THE DRAWINGS

FIG. 2 is a flowchart for explaining a flow of overall processes executed in the operation control device according to the present embodiment;

FIG. 3 is a flowchart for explaining a flow of indirect execution mode processes executed in the operation control device according to the present embodiment;

FIG. 5 is a flowchart for explaining a flow of an abstract image updating processing executed in the operation control device according to the present embodiment.

DETAILED DESCRIPTION OF THE INVENTION

An exemplary embodiment of an operation control device, an operation control method, and a program is described below in detail with reference to the accompanying drawings. However, the present application is not limited by the embodiment described below.

<Operation Control Device>

Figure 1:
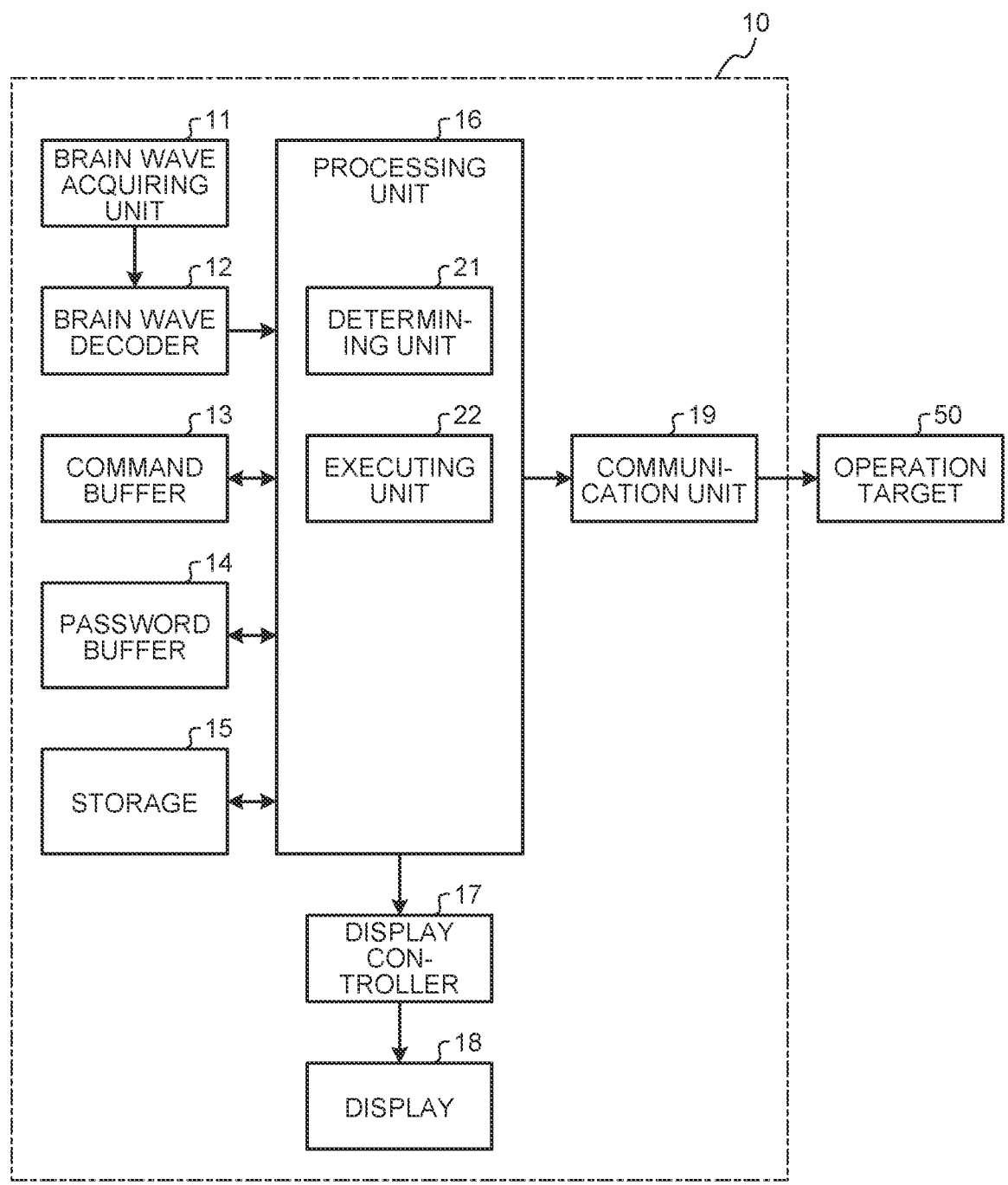
FIG. 1 is a block diagram illustrating an exemplary configuration of an operation control device according to an embodiment.

FIG. 1 is a block diagram illustrating an exemplary configuration of the operation control device according to the present embodiment.

In the present embodiment, as illustrated in FIG. 1, based on brain information of a user, an operation control device 10 executes operation control with respect to an operation target 50. The operation control device 10 includes a brain wave acquiring unit (a brain information acquiring unit) 11, a brain wave decoder 12, a command buffer 13, a password buffer 14, a storage 15, a processing unit 16, a display controller 17, a display 18, and a communication unit 19.

An operation target 50 is, for example, a robot. However, the operation target 50 is not limited thereto, and, as long as a device that operates based on communication is used, it serves the purpose. Although not illustrated in FIG. 1, the operation target 50 includes a driving device, a controller that controls the driving device, and a communication unit that is capable of receiving control signals. In the operation target 50, when the communication unit receives a control signal, the control device drives the driving device and brings the robot into operation.

The brain wave acquiring unit 11 can be attached to a head region of the user. As far as the brain wave decoder 12, the processing unit 16, the display controller 17, the display 18, and the communication unit 19 are concerned, either they can be attached to the user or they can be disposed at a predetermined position without being worn by the user. Moreover, the brain wave decoder 12, the processing unit 16, the display controller 17, the display 18, and the communication unit 19 either can be installed in an integrated manner or can be installed as separate units.

The brain wave acquiring unit 11 acquires brain waves that represent brain information of the user. For example, the brain wave acquiring unit 11 includes an electrical sensor (for example, an electrode) that detects the brain waves deriving from a weak electrical current flowing in a neural network of the brain. The brain wave acquiring unit 11 detects an electrical potential (electrical signals) of the weak electrical current generated when the user receives an external stimulus or generated on thoughts of the user such as contemplation. Meanwhile, the brain information acquiring unit is not limited to be the brain wave acquiring unit 11. Alternatively, for example, the brain information acquiring unit can acquire a blood flow volume, which is attributed to a brain activity representing the brain information of the user, with a near-infrared light measurement, for example. The brain wave acquiring unit 11 is connected to the brain wave decoder 12 and sends, to the brain wave decoder 12, the brain waves representing the brain information acquired from the user.

The brain wave decoder 12 decodes the electrical signals of the brain waves of the user, which are acquired by the brain wave acquiring unit 11, to contemplation information. In that case, multiple electrical signals of the brain waves of the user is associated in advance to the contemplation information of the user. For example, the electrical signals of the brain waves are associated to pieces of the contemplation information of the user using machine learning based on deep learning.

The command buffer 13 is used to temporarily store first commands that are determined by a determining unit 21 based on the contemplation information of the user. The first command is a command for operating the operation target 50, and examples thereof include "forward movement", "backward movement", "halting", "acceleration", "deceleration", "clockwise turning", and "counterclockwise turning". In those cases, each first command is associated in advance to operation of the operation target 50. Meanwhile, the command buffer 13 is capable of sending a variety of data to and receiving a variety of data from the processing unit 16.

The first command is not limited to a concept indicating operation to be instructed. Alternatively, a first command can have a numerical value added thereto for complementing to the concept indicating the operation to be instructed. For example, based on the electrical signals acquired by the brain wave acquiring unit 11, the brain wave decoder 12 can decode the contemplation information of the user, detect an intensity of the brain waves in a form of a decimal between 0 and 1, and set a first command in which the intensity (numerical value) is added to the contemplation information. In that case, the numerical value of the first command represents a maximum torque output counted in the driving device installed in the operation target 50.

The password buffer 14 is used to temporarily store passwords representing second commands determined by the determining unit 21 based on the contemplation information of the user. A password representing a second command is used in deciding to execute a first command. A password is made of a combination of one or more symbols that are used in forming the password. Meanwhile, the password buffer 14 is capable of sending a variety of data to and receiving a variety of data from the processing unit 16.

The storage 15 is used to store multiple first commands and multiple second commands. Moreover, the storage 15 can be used to store learning data that is acquired as a result of executing machine learning of a relationship between the electrical signals of the brain waves of the user and the contemplation information of the user. Meanwhile, a second command is made of multiple symbols used in forming a password. The storage 15 is capable of sending a variety of data to and receiving a variety of data from the processing unit 16. The processing unit 16 sets or updates a password by combining one or more symbols from among multiple symbols stored in the storage 15. Meanwhile, as far as the passwords are concerned, either a common password can be set across different first commands, or an individual password can be set for each of the different first commands.

The password as a second command is an abstract image. Since the password is made of a combination of one or more symbols, thus the symbol is an abstract image. An abstract image can be a symbol such as "Δ", "□", or "×", or a color such as "red", "blue", or "black", or a number such as "0", "1", or "2", or an article or a scenery. Thus, for example, "Δ"+"red"+"9" can be set as a password as a second command.

The command buffer 13 as well as the password buffer 14 is a semiconductor memory device such as a RAM (Random Access Memory) or a flash memory. The storage 15 is configured using a memory card, an SSD (Solid State Drive), or an external memory device.

The processing unit 16 is capable of switching between a direct execution mode and an indirect execution mode. In the direct execution mode, when a first command for causing the processing unit 16 to bring the operation target 50 into operation is input, the processing unit 16 executes the first command. On the other hand, in the indirect execution mode, when a first command as well as a second command is input for causing the processing unit 16 to bring the operation target 50 into operation, the processing unit 16 executes the first command.

The processing unit 16 is, for example, an arithmetic processing device (a control device) configured using a CPU (Central Processing Unit). The processing unit 16 loads a stored program into a memory and executes the commands specified in the program. The processing unit 16 includes an internal memory (not illustrated) that is used to temporarily store data. The processing unit 16 is configured to function as the determining unit 21 and an executing unit 22. The processing unit 16 sends the processing result to the display controller 17 and the communication unit 19.

The determining unit 21 determines whether or not the contemplation information of the user, which is acquired by the brain wave acquiring unit 11 and decoded by the brain wave decoder 12, represents the brain waves corresponding to a first command and a second command (password) that are different from each other.

More particularly, the determining unit 21 compares the contemplation information of the user, which is decoded by the brain wave decoder 12, with a first command stored in the storage 15. If the contemplation information of the user matches with a first command, then the determining unit 21 determines that the contemplation information of the user represents a first command. Thus, the determining unit 21 stores, in the command buffer 13, the command determined to be a first command. On the other hand, if the contemplation information of the user does not match with any first command, then the determining unit 21 determines that the contemplation information of the user does not represent a first command. Thus, the determining unit 21 does not store, in the command buffer 13, the command determined not to be a first command. Regarding the determination executed by the determining unit 21 about whether or not the contemplation information of the user, which is decoded by the brain wave decoder 12, matches with a first command, it is determined to match with a first command even if it does not match therewith completely as long as it can be determined to imply a first command.

Moreover, the determining unit 21 compares the contemplation information of the user, which is decoded by the brain wave decoder 12, with the passwords stored in the storage 15. If the contemplation information of the user matches either with a password or with symbols constituting a password, then the determining unit 21 determines that the contemplation information of the user represents either a password or symbols constituting the password. If the contemplation information of the user is determined to represent a password or symbols, then the determining unit 21 stores the password or the symbols in the password buffer 14. On the other hand, if the contemplation information of the user does not match with any stored password or with the symbols constituting a password, then the determining unit 21 determines that the contemplation information of the user neither represents a password nor represents symbols constituting the password. When the contemplation information of the user is determined not to represent a password or symbols, no passwords or symbols are stored in the password buffer 14.

When the determining unit 21 determines that the brain wave corresponding to a first command and the brain wave corresponding to a password are acquired, the executing unit 22 executes the operation specified in the first command. More particularly, when the determining unit 21 determines that the initially-acquired contemplation information of the user represents a first command and determines that the subsequently-acquired contemplation information of the user represents a password, the executing unit 22 executes the operation specified in the first command.

However, after the determining unit 21 determines that a first command is acquired, when a preset standby period such as three seconds elapses, then the executing unit 22 cancels the acquired first command. Moreover, after the determining unit 21 determines that a first command is acquired, when the processing unit 16 acquires a cancel command as the contemplation of the user, then the executing unit 22 cancels the acquired first command. Herein, a cancel command is a preset command, and the electrical signals of the brain waves of the user are associated to the contemplation information (cancel command) of the user and the associated information is stored in the storage 15.

Thus, when the direct execution mode is selected, if the determining unit 21 determines that the contemplation information of the user represents a first command, the executing unit 22 executes the first command without determining whether or not a second command is input. On the other hand, when the indirect execution mode is selected, if the determining unit 21 determines that the contemplation information of the user represents a first command, the executing unit 22 does not execute the first command right away. That is, after determining that the initial contemplation information of the user represents a first command, if the determining unit 21 determines that the subsequent contemplation information of the user represents a second command (password), then the executing unit 22 executes the first command.

The display controller 17 and the display 18 function as an information providing unit that provides a variety of information. When the determining unit 21 determines that the brain waves corresponding to a first command are acquired, the display controller 17 and the display 18 present information evoking the password. In the present embodiment, the information presenting unit presents information which evokes a password to the user by visual information. However, that is not the only possible case. For example, the information presenting unit may present information which evokes a password by sound information. In that case, the information presenting unit is composed of, for example, a sound output controller and a speaker.

The display controller 17 is connected to the display 18. The display controller 17 sends the processing result, which is sent from the processing unit 16, to the display 18 for displaying the processing result. Thus, the display controller 17 displays, in the display 18, the processing result acquired by the processing unit 16, such as the operating state of the operation control device 10 or a contemplation instruction with respect to the user.

The processing unit 16 controls the display controller 17 and causes it to display necessary information in the display 18. Thus, the processing unit 16 controls the display controller 17 and causes it to display, in the display 18, an instruction to the user for evoking the symbol (the abstract image) of the password representing a second command. Since the symbol is an abstract image, the display 18 either can display the actual abstract image or can display an image or a word that evokes the abstract image.

The display 18 is used to display the operating state of the operation control device 10 or a contemplation instruction for the user sent from the display controller 17. Thus, the display 18 presents the necessary information to the user. The display 18 is, for example, a display such as a liquid crystal display (LCD) or an organic EL (Organic Electro-Luminescence) display.

The communication unit 19 is capable of executing wireless communication with the operation target 50. The communication unit 19 sends, to the operation target 50, processed information that is acquired by the processing unit 16 as a result of executing processing. More particularly, when the determining unit 21 determines that the brain waves corresponding to a first command and the brain waves corresponding to a password are acquired, the executing unit 22 generates a control signal corresponding to operation specified in the first command and sends the control signal to the communication unit 19. Then, the communication unit 19 sends, to the operation target 50, the control signal corresponding to the operation specified in the first command. The operation target 50 receives the first command sent by the communication unit 19, and operates according to the operation specified in the first command.

<Operation Control Method>

Given below is an explanation of an operation control method implemented in the operation control device 10.

FIG. 2 is a flowchart for explaining a flow of the overall processes executed in the operation control device according to the present embodiment.

As illustrated in FIGS. 1 and 2, at Step S11, the processing unit 16 determines whether or not the contemplation information of the user, which is acquired by the brain wave acquiring unit 11 and decoded by the brain wave decoder 12, indicates a mode switching command. If it is determined that the contemplation information of the user indicates a mode switching command (Yes), then, at Step S12, the processing unit 16 switches the mode. That is, if the direct execution mode is currently set, then the processing unit 16 switches the mode to the indirect execution mode. On the other hand, if the indirect execution mode is currently set, then the processing unit 16 switches the mode to the direct execution mode. At that time, the processing unit 16 controls the display controller 17 and causes it to display, in the display 18, the fact indicating to the user that the mode has been switched. For example, when the mode is switched to the direct execution mode, the display controller 17 displays the operation content indicating "the mode is switched to the direct execution mode" in the display 18. On the other hand, when the mode is switched to the indirect execution mode, the display controller 17 displays the operation content indicating "the mode is switched to the indirect execution mode" in the display 18. Thus, the display controller 17 notifies the user about the switch in the mode. Then, at Step S13, the command buffer 13 and the password buffer 14 are cleared, and the present routine is exited.

Meanwhile, at Step S11, if it is determined that the contemplation information of the user does not indicate a mode switching command (No), then, at Step S14, the processing unit 16 determines whether or not the direct execution mode is currently selected. If the processing unit 16 determines that the direct execution mode is currently selected (Yes), then, at Step S15, the determining unit 21 determines whether or not the contemplation information of the user, which is acquired by the brain wave acquiring unit 11 and decoded by the brain wave decoder 12, represents the brain waves corresponding to a first command. If the determining unit 21 determines that the contemplation information of the user does not represent a first command (No), then the present routine is exited.

On the other hand, at Step S15, if the determining unit 21 determines that the contemplation information of the user represents a first command (Yes), then, at Step S16, the executing unit 22 executes the operation specified in the first command. That is, using the communication unit 19, the executing unit 22 sends, to the operation target 50, a control signal corresponding to the operation specified in the first command and brings the operation target 50 into operation. At that time, the processing unit 16 controls the display controller 17 and causes it to display, in the display 18, the fact indicating to the user that the first command has been executed. For example, the display controller 17 displays, in the display 18, a message such as "acceleration command was executed" indicating the fact that the first command was executed.

Meanwhile, at Step S14, if it determined that the direct execution mode is not currently selected (No), then, at Step S17, the processing unit 16 executes the operations corresponding to the indirect execution mode. The operations illustrated in FIG. 2 are executed in a repeated manner during the period in which the operation of the operation target 50 is controlled by the operation control device 10.

Given below is an explanation of processes executed in the indirect execution mode. FIG. 3 is a flowchart for explaining a flow of the indirect execution mode processes executed in the operation control device according to the present embodiment.

As illustrated in FIGS. 1 and 3, at Step S21, the determining unit 21 determines whether or not the contemplation information of the user, which is acquired by the brain wave acquiring unit 11 and decoded by the brain wave decoder 12, represents the brain waves corresponding to a first command. If it is determined that the contemplation information of the user represents a first command (Yes), then, at Step S22, the determining unit 21 stores the first command in the command buffer 13. At that time, the processing unit 16 can control the display controller 17 and cause it to display, in the display 18, the fact indicating to the user that the first command has been stored. For example, the display controller 17 displays, in the display 18, a message such as "acceleration command was stored" indicating the fact that the first command was stored. Then, at Step S23, the password buffer 14 is cleared.

Meanwhile, at Step S21, if it is determined that the contemplation information of the user does not represent a first command (No), then, at Step S24, the determining unit 21 determines whether or not any first command is stored in the command buffer 13. If it is determined that a first command is stored in the command buffer 13 (Yes), then, at Step S25, the determining unit 21 executes an abstract image processing.

Figure 4:
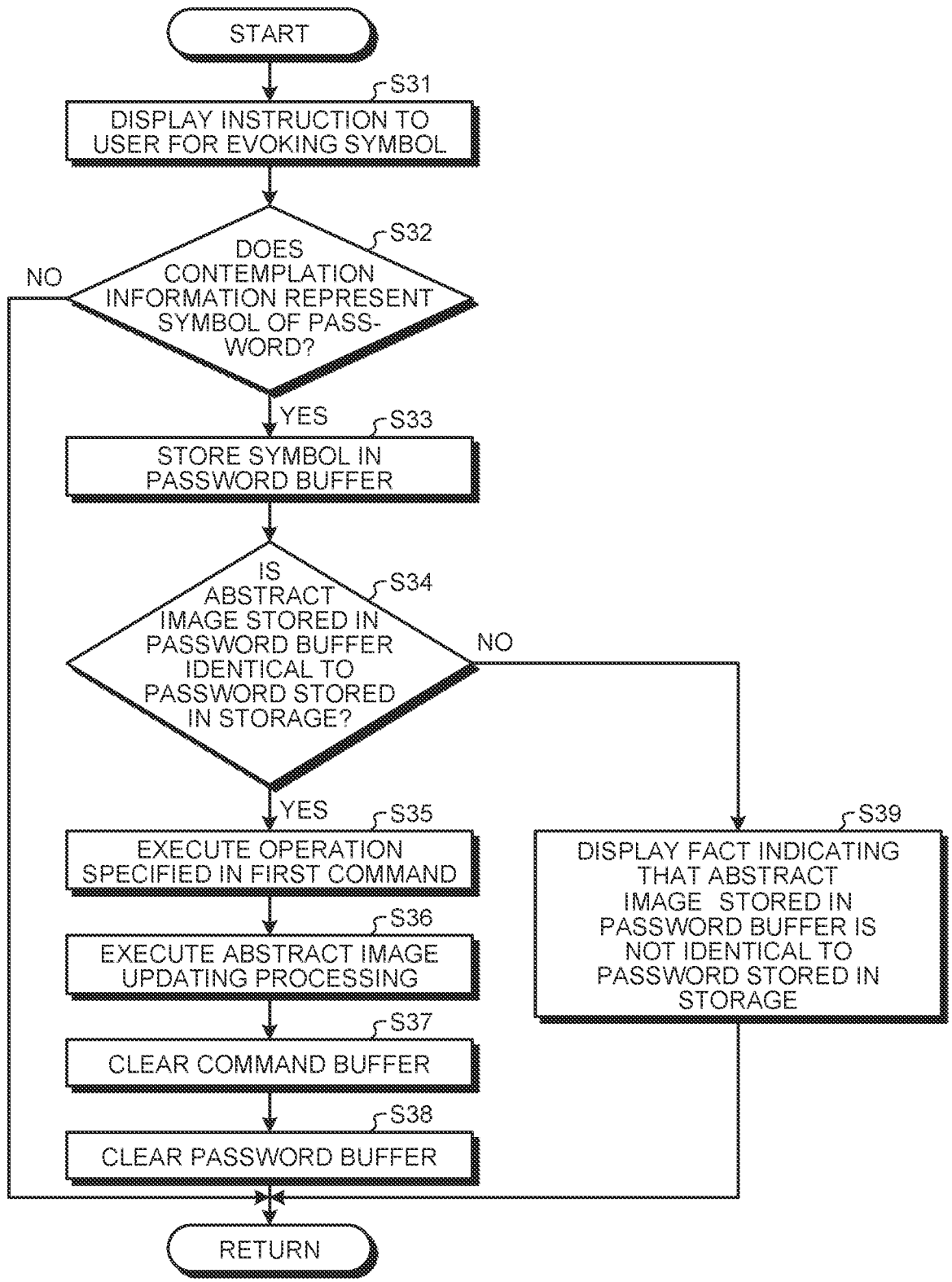
FIG. 4 is a flowchart for explaining a flow of abstract image process executed in the operation control device according to the present embodiment.

Given below is an explanation about an abstract image processing. FIG. 4 is a flowchart for explaining a flow of the abstract image processing executed in the operation control device according to the present embodiment.

As illustrated in FIGS. 1 and 4, at Step S31, the processing unit 16 controls the display controller 17 and causes it to display, in the display 18, an instruction to the user for evoking a symbol (an abstract image) of the password representing a second command. For example, the display controller 17 displays an image equivalent to an abstract image in the display 18.

At Step S32, the determining unit 21 determines whether or not the contemplation information of the user, which is acquired by the brain wave acquiring unit 11 and decoded by the brain wave decoder 12, represents the brain waves corresponding to a password (an abstract image). If the determining unit 21 determines that the contemplation information of the user does not represent a password (an abstract image) (No), then the present routine is exited.

On the other hand, if it is determined that the contemplation information of the user represents a symbol of a password (Yes), then, at Step S33, the determining unit 21 stores the symbol as a single abstract image in the password buffer 14. However, if the determining unit 21 determines that the contemplation information of the user does not represent a symbol of a password (No), then the present routine is exited.

At Step S34, the determining unit 21 compares the abstract image stored in the password buffer 14 with a password composed of one or more abstract images stored in the storage 15, and determines whether or not they are identical. If the determining unit 21 determines that the abstract image stored in the password buffer 14 is not identical to the password composed of the abstract image stored in the storage 15 (No), then, at Step S39, the processing unit 16 controls the display controller 17 and displays, in the display 18, the fact indicating to the user that the abstract image stored in the password buffer 14 is not identical to the password stored in the storage 15.

On the other hand, at Step S34, if the determining unit 21 determines that the abstract image stored in the password buffer 14 is identical to the password composed of one or more abstract images stored in the storage 15 (Yes), then, at Step S35, the executing unit 22 executes the operation specified in the first command stored in the command buffer 13. That is, using the communication unit 19, the executing unit 22 sends, to the operation target 50, a control signal corresponding to the operation specified in the first command and brings the operation target 50 into operation. At that time, the processing unit 16 controls the display controller 17 and causes it to display, in the display 18, the fact indicating to the user that the first command has been executed. For example, the display controller 17 displays, in the display 18, a message such as "acceleration command was executed" indicating the fact that the first command was executed.

At Step S36, the processing unit 16 executes an abstract image updating processing for a purpose of updating the password. Regarding the abstract image updating processing, an explanation is given below. Subsequently, at Step S37, the command buffer 13 is cleared, and, at Step S38, the password buffer 14 is cleared.

The following explanation is given about the abstract image updating processing. FIG. 5 is a flowchart for explaining a flow of the abstract image updating processing executed in the operation control device according to the present embodiment.

When operation for comparing the password (the abstract image) evoked by the user and the preset password (the abstract image) is executed many times, the user ends up remembering the preset password (the abstract image). Hence, it becomes less meaningful to input a password for expressing the intention of executing the operation content corresponding to the first command. That is, the user ends up executing the first command with ease. For that reason, when a predetermined condition is satisfied, the processing unit 16 executes the abstract image updating processing for updating and changing the password.

As illustrated in FIGS. 1 and 5, at Step S41, the processing unit 16 determines whether or not a predetermined condition for updating the password is satisfied. If the processing unit 16 determines that the predetermined condition is not satisfied (No), then the present routine is exited. On the other hand, if it is determined that the predetermined condition is satisfied (Yes), then, at Step S42, the processing unit 16 adds a symbol of a necessary abstract image to the current password to update the password.

Examples of the predetermined condition for updating the password include a condition in which an execution count of the first command exceeds a predetermined count, a condition in which an intensity of the brain waves processed by the brain wave decoder 12 exceed a predetermined level, and a condition in which operation of adding the necessary abstract images is input by an input means such as the brain waves.

Meanwhile, in the embodiment described above, a first command and a second command (password) are detected in chronological order. However, that is not the only possible configuration. For example, a first command as well as a second command (password) can be detected at the same time. That is, the processes from Step S21 to Step S23 illustrated in FIG. 3 can be executed in parallel to the processes from Step S31 to Step S34 illustrated in FIG. 4.

In the present embodiment, the operation control device includes: the brain wave acquiring unit (brain information acquiring unit) 11 that acquires the brain information of the user; the determining unit 21 that determines whether or not the brain information acquired by the brain wave acquiring unit 11 represents brain information corresponding to a first command and a second command that are different from each other; the display controller 17 and the display as an information presenting unit that presents information evoking the second command; and the executing unit 22 that, when the determining unit 21 determines that the brain information corresponding to the first command and the brain information corresponding to the second command is acquired, executes the operation specified in the first command.

Thus, when the brain information corresponding to the first command and the brain information corresponding to the second command are acquired, the operation specified in the first command is executed and the operation target 50 is brought into operation. That is, even when the brain information corresponding to the first command representing the operation content is acquired, unless the brain information corresponding to the second command expressing the intention to execute the operation content is acquired, the operation specified in the first command is not executed. Hence, the content and the execution timing of the first command are implemented in a safer and more precise manner, thereby making it possible to execute an appropriate brain wave command without being impacted by any irrelevant stimulus.

Moreover, in the present embodiment, the display controller 17 and the display 18 as the information presenting unit presents, to the user, the information evoking a second command. That enables the user to evoke the second command. Thus, the first command can be appropriately executed without the user remembering the second command.

Furthermore, in the present embodiment, a first command represents the operation content for operating the operation target 50, and a second command represents the intention of implementing the operation content with respect to the operation target 50. Thus, when the brain information corresponding to a second command is acquired, it becomes possible to confirm the intention of the user to implement the operation content with respect to the operation target 50, and to execute an appropriate brain wave command.

Furthermore, in the present embodiment, the determining unit 21 can set a second command to notify the user of the set second command by the display controller 17 and the display 18 as the information presenting unit, and can change the second command when a preset updating condition is satisfied. If the same second command is used over a long time period, the user ends up remembering the second command. That makes it less meaningful to confirm the intention of the user to execute the operation content corresponding to the first command. In that regard, by changing the second command, it becomes possible to appropriately confirm the intention of the user to execute the operation content.

In the above, the explanation was given about the operation control device 10 according to the present application. However, the present application can be implemented in various other forms other than the embodiment described above.

The constituent elements of the operation control device 10 illustrated in the drawings are merely conceptual, and need not be physically configured as illustrated. The constituent elements, as a whole or in part, can be separated or integrated either functionally or physically based on various types of loads or use conditions.

The configuration of the operation control device 10 is implemented by, for example, a program that is loaded as software in a memory. In the embodiment described above, the configuration is explained with function blocks implemented by a combination of hardware and software. That is, such function blocks can be implemented in various ways, such as using only hardware, or using only software, or using a combination of hardware and software.

According to the present application, it becomes possible to execute appropriate brain wave commands without being impacted by any irrelevant stimulus.

Although the present application has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

The operation control device, the operation control method, and the program according to the present application can be implemented in, for example, a brain-machine-interface.

What is claimed is:

1. An operation control device comprising:
   a display;
   a memory that is configured to store computer executable instructions; and
   a processor that is configured to execute the computer executable instructions to perform operations, the operations comprising:
      acquiring brain information of a user based on brain waves;
      determining whether the brain information comprises brain information corresponding to a first command and brain information corresponding to a second command that is different from the first command;
      presenting information that evokes the second command to the user by the display; and
      executing an operation specified in the first command in response to a determination that the brain information corresponding to the second command is acquired after acquiring the brain information corresponding to the first command, wherein
   the second command is an abstract image to decide to execute the operation specified by the first command and set by the processor, and
   the determining comprises:
      setting the second command;
      notifying the user of the second command by the display; and
      changing the second command in response to determining that a predetermined updating condition is satisfied, wherein the predetermined updating condition includes at least one of a condition in which an execution count of the first command exceeds a predetermined count, a condition in which an intensity of the brain waves exceeds a predetermined level, or a condition in which operation of adding a necessary abstract image that evokes the second command is input by the brainwaves.

2. The operation control device according to claim 1, wherein
   the first command represents operation content for operating an operation target, and
   the abstract image indicates intention of executing the operation content for the operation target.

3. The operation control device according to claim 1, the operations further comprising, in response to acquisition of the brain information corresponding to the first command, causing the display to display information that evokes the second command to the user.

4. An operation control method comprising:
   acquiring brain information of a user;
   determining whether the acquired brain information comprises brain information corresponding to a first command and brain information corresponding to a second command, wherein the second command is different from the first command;
   presenting information that evokes the second command to the user by a display; and
   executing an operation specified in the first command in response to a determination that the brain information corresponding to the second command is acquired after acquiring the brain information corresponding to the first command, wherein
   the second command is an abstract image to decide to execute the operation specified by the first command and set by a device in which the method is performed, and
   the determining comprises:
      setting the second command;
      notifying the user of the second command by the display; and
      changing the second command in response to determining that a predetermined updating condition is satisfied, wherein the predetermined updating condition includes at least one of a condition in which an execution count of the first command exceeds a predetermined count, a condition in which an intensity of the brain waves exceeds a predetermined level, or a condition in which operation of adding a necessary abstract image that evokes the second command is input by the brain waves.

5. A non-transitory storage medium that stores a program that causes a computer to execute:
   acquiring brain information of a user;
   determining whether the brain information comprises brain information representing a first command and brain information representing a second command that is different from the first command;
   presenting information that evokes the second command to the user by a display; and
   executing an operation specified in the first command in response to a determination that the brain information representing the second command is acquired after acquiring the brain information representing the first command, wherein
   the second command is an abstract image to decide to execute the operation specified by the first command and set by a device in which the method is performed, and
   the determining comprises:
      setting the second command;
      notifying the user of the second command by the display; and
      changing the second command in response to determining that a predetermined updating condition is satisfied, wherein the predetermined updating condition includes at least one of a condition in which an execution count of the first command exceeds a predetermined count, a condition in which an intensity of the brain waves exceeds a predetermined level, or a condition in which operation of adding a necessary abstract image that evokes the second command is input by the brain waves.

\* \* \* \* \*